United States Patent
Li et al.

(10) Patent No.: US 12,117,449 B2
(45) Date of Patent: Oct. 15, 2024

(54) USE OF BAZ1B_K426HY AND POLYCLONAL ANTIBODY THEREOF IN PREPARATION OF PRODUCT FOR TUMOR DETECTION

(71) Applicants: Tangshan People's Hospital, Hebei (CN); North China University of Science and Technology, Hebei (CN); Tangshan Maternal And Child Health Hospital, Hebei (CN)

(72) Inventors: Jingwu Li, Tangshan (CN); Yufeng Li, Tangshan (CN); Shuqing Wang, Tangshan (CN); Jinghua Zhang, Tangshan (CN); Jinghua Wu, Tangshan (CN); Fen Hu, Tangshan (CN); Yuan Yu, Tangshan (CN); Yan Liu, Tangshan (CN); Yuhui Li, Tangshan (CN); Xuan Zheng, Tangshan (CN)

(73) Assignees: Tangshan People's Hospital, Tangshan (CN); North China University of Science and Technology, Tangshan (CN); Tangshan Maternal And Child Health Hospital, Tangshan (CN)

( * ) Notice: Subject to any disclaimer, the term of this patent is extended or adjusted under 35 U.S.C. 154(b) by 0 days.

(21) Appl. No.: 18/301,141

(22) Filed: Apr. 14, 2023

(65) Prior Publication Data

US 2024/0133890 A1 Apr. 25, 2024
US 2024/0230653 A9 Jul. 11, 2024

(30) Foreign Application Priority Data

Oct. 21, 2022 (CN) .......................... 202211290030.1

(51) Int. Cl.
*G01N 33/574* (2006.01)
*C07K 16/32* (2006.01)

(52) U.S. Cl.
CPC ....... *G01N 33/57484* (2013.01); *C07K 16/32* (2013.01); *G01N 2800/7028* (2013.01)

(58) Field of Classification Search
CPC ..... G01N 33/57484; G01N 2800/7028; C07K 16/32
See application file for complete search history.

(56) References Cited

PUBLICATIONS

First Office Action of the China National Intellectual Property Administration (CNIPA) dated Jun. 9, 2023, in related Chinese Appl. No. 202211290030.1, 14 pages.
Yuanyue, Z. "JMJD6 Regulates Breast Cancer Cell Activity via WSTF", North China University of Science and Technology, 62 pages, Jun. 2021.
"Quality Management of Hospital Clinical Laboratory (Laboratory)", Hospital clinical examination technology operation standard and practical laboratory management, vol. 1, Chapter 2, p. 112.

*Primary Examiner* — Mark Halvorson
*Assistant Examiner* — Dennis J Sullivan
(74) *Attorney, Agent, or Firm* — Bochner PLLC; Andrew D. Bochner

(57) ABSTRACT

The present disclosure provides the use of BAZ1B_K426hy in the preparation of a product for tumor detection and belongs to the field of biotechnology. The present disclosure further provides a group of immunogenic polypeptides, including polypeptide A and polypeptide B. An anti-BAZ1B_K426hy polyclonal antibody is prepared by conducting mixed immunization on an animal with the immunogenic polypeptide. The polyclonal antibody can specifically recognize an endogenous protein BAZ1B_K426hy by enzyme-linked immunosorbent assay (ELISA)/Dot blot/Western blot, which is used for preparation of detection products for tumors and Williams syndrome.

2 Claims, 6 Drawing Sheets
Specification includes a Sequence Listing.

USE OF BAZ1B_K426HY AND POLYCLONAL ANTIBODY THEREOF IN PREPARATION OF PRODUCT FOR TUMOR DETECTION

CROSS-REFERENCE TO RELATED APPLICATION

This patent application claims the benefit and priority of Chinese Patent Application No. 202211290030.1 filed with the China National Intellectual Property Administration on Oct. 21, 2022, the disclosure of which is incorporated by reference herein in its entirety as part of the present application.

REFERENCE TO SEQUENCE LISTING

A computer readable XML file entitled "GWP20220602662-Sequence listing.xml", that was created on Dec. 19, 2022, with a file size of about 4,055 bytes, contains the sequence listing for this application, has been filed with this application, and is hereby incorporated by reference in its entirety.

TECHNICAL FIELD

The present disclosure belongs to the field of biotechnology and particularly relates to the use of BAZ1B_K426hy and a polyclonal antibody thereof in the preparation of a product for tumor detection.

BACKGROUND

The BAZ1B gene (also known as the WSTF gene), is a gene encoding the transcription factor BAZ1B detected in patients with Williams syndrome. Williams syndrome is a genetic disorder with more than 20 genes known to be associated with its pathogenesis. The studies have found that the BAZ1B gene plays a more important role than other genes in a series of systemic defects exhibited by patients. The researchers have found that BAZ1B-knockout mice are smaller than normal control mice and die within a few days of birth, suggesting that the gene plays an important role in the normal growth and development of the mouse. Further mechanistic studies have revealed that the BAZ1B protein has highly diverse functions and participates in biological processes including chromatin remodeling, gene transcription and expression regulation, cell cycle and apoptosis regulation, DNA damage repair, and vitamin metabolism. In terms of gene transcription regulation, BAZ1B has a particularly complex way of participation. The BAZ1B protein is detected in all three important ATP-dependent chromatin remodeling complexes, acting as both transcriptional activation and repression. Therefore, BAZ1B is considered to be at the core of chromatin regulation.

At present, studies have shown that BAZ1B can bind to a secreted protein neuregulin-3 (NRG3) and be transported out of cells to promote the occurrence and development of colon cancer through a paracrine approach. Other studies have clarified that BAZ1B regulates the occurrence and development of breast cancer and lung cancer by promoting cell proliferation and migration. The introduction of BAZ1B into oncology has attracted close attention in the field. BAZ1B belongs to the bromodomain adjacent to a zinc-finger domain (BAZ), a protein family that has multiple domains (FIG. 1) and diverse biological functions. BAZ1B can recognize and bind to histones through the PHD (plant homeodomain), WAC (WSTF/Acf1/cbpq46), and Bromodomain, participating in the regulation of histone modifications. The WAC of BAZ1B has tyrosine kinase activity and can phosphorylate the tyrosine residue 142 of histone H2A.X, which is involved in repair or apoptosis regulation after DNA damage. Proteins containing the PHD are generally able to bind to methylated Lys residues (K, Lysine) and regulate gene transcription. However, the histone modification site that specifically binds to the PHD of WSTF has not been identified. The Bromodomain of WSTF can bind to acetylated histones (such as H3K14Ac, H4K16Ac, and H2BK12Ac) to regulate the transcription of downstream target genes.

The function of BAZ1B in promoting proliferation and migration of breast cancer cells is regulated by the type and level of its post-translational modifications, and BAZ1B can undergo multiple post-translational modifications at multiple sites. In breast cancer cells, it has been identified that Ser158 (S, Serine) and Lys426 residues of BAZ1B can undergo phosphorylation (S158ph) and acetylation (K426Ac) modifications, respectively. However, both phosphorylation of Ser158 residue and acetylation of Lys426 residue positively regulate the BAZ1B activity. Negative regulatory signals also play an important role in regulating protein functions. In a certain spatiotemporal-specific context, the balance of negative and positive regulations can keep cells and tissues in a normal and stable state. However, currently, there are no related reports on other modification sites of BAZ1B and corresponding polyclonal antibodies/immunogenic polypeptides.

SUMMARY

An objective of the present disclosure is to provide the use of BAZ1B_K426hy in the preparation of a product for tumor detection, and the occurrence of tumor cells can be diagnosed by an expression level of BAZ1B_K426hy.

The objective of the present disclosure is to further provide an immunogenic polypeptide, which can be used to prepare an anti-BAZ1B_K426hy polyclonal antibody.

The objective of the present disclosure is to further provide an anti-BAZ1B_K426hy polyclonal antibody, which can specifically recognize an endogenous protein BAZ1B_K426hy through ELISA/Dot blot/Western blot.

To achieve the above objectives, the present disclosure provides the following technical solutions.

The present disclosure provides the use of BAZ1B_K426hy in the preparation of a product for tumor detection.

Preferably, the product includes an antibody, a drug, and a kit.

Preferably, the tumor includes lung cancer, triple-negative breast cancer, non-triple-negative breast cancer, colorectal cancer, melanoma, gastric cancer, cervical cancer, glioma, esophageal cancer, ovarian cancer, and pancreatic cancer.

The present disclosure further provides an immunogenic polypeptide for preparing an anti-BAZ1B_K426hy polyclonal antibody, where the polypeptide includes polypeptide A with a sequence of SKSPK-hydroxyl K-GLKTP and polypeptide B with a sequence of NSKSPK-hydroxyl K-GLKTPK.

The present disclosure further provides an anti-BAZ1B_K426hy polyclonal antibody, where the polyclonal antibody is obtained by conducting mixed immunization on an animal with the immunogenic polypeptide.

Preferably, polypeptide A and polypeptide B are separately coupled to keyhole limpet hemocyanin (KLH) to conduct mixed immunization.

Preferably, a solution of coupled polypeptide A and a solution of coupled polypeptide B are mixed in a volume ratio of (1-2):(1-2).

Preferably, the animal is a rabbit.

The present disclosure further provides a method for preparing the polyclonal antibody, including the following steps: coupling polypeptide A and polypeptide B of the immunogenic polypeptide to KLH separately; mixing two solutions of coupled polypeptides in a volume ratio of (1-2):(1-2) to conduct animal immunization; collecting serum of an immunized animal and conducting purification to obtain the anti-BAZ1B_K426hy polyclonal antibody.

Preferably, the animal immunization is conducted 3 to 5 times.

Compared with the prior art, the present disclosure has the following beneficial effects.

In the present disclosure, it is found that the Lys426 residue of BAZ1B can also undergo hydroxylation modification in tumor cells and has a competitive relationship with acetylation modification at the same site. The expression level of BAZ1B_K426hy protein in tumor cells is significantly different from that in normal cells, such that the occurrence of tumor cells can be diagnosed by the expression level of BAZ1B_K426hy.

In the present disclosure, the immunogenic polypeptide has excellent immunogenicity.

The anti-BAZ1B_K426hy polyclonal antibody obtained by immunizing animals with the polypeptide has desirable affinity and can specifically recognize an endogenous protein BAZ1B_K426hy by ELISA/Dot blot/Western blot. The polyclonal antibody has high specificity, excellent sensitivity, and desirable titer, which can be used for the preparation of detection reagents for BAZ1B_K426hy protein-related diseases.

DETAILED DESCRIPTION OF THE EMBODIMENTS

The present disclosure provides the use of BAZ1B_K426hy in the preparation of a product for tumor detection.

In the present disclosure, the BAZ1B_K426hy refers to a protein modified by hydroxylation (hy) of a Lys426 residue of WSTF (BAZ1B). In the present disclosure, it is found that the Lys426 residue of BAZ1B can also undergo hydroxylation modification in tumor cells, and has a competitive relationship with acetylation modification at the same site. Hydroxylation of the Lys426 may be a negative regulatory modification of BAZ1B protein, and the hydroxylation of this site can inhibit the transcriptional regulatory activity of WSTF and induce its degradation. The expression level of BAZ1B_K426hy protein in the tumor cells is significantly different from that in the normal cells, such that the occurrence of tumor cells can be diagnosed by the expression level of BAZ1B_K426hy.

In the present disclosure, the product includes an antibody, a drug, and a kit. The tumor includes lung cancer, triple-negative breast cancer, non-triple-negative breast cancer, colorectal cancer, melanoma, gastric cancer, cervical cancer, glioma, esophageal cancer, ovarian cancer, and pancreatic cancer. The expression levels of BAZ1B_K426hy in lung cancer cells, triple-negative breast cancer cells, non-triple-negative breast cancer cells, colorectal cancer cells, melanoma cells, gastric cancer cells, cervical cancer cells, glioma cells, esophageal cancer cells, ovarian cancer cells, and pancreatic cancer cells were compared with the expression levels of BAZ1B_K426hy in lung epithelial cells and ovarian epithelial cells in normal cells. It is found that there are significant differences in the expression levels of BAZ1B_K426hy in tumor cells and normal cells, such that the occurrence of tumors can be determined by detecting the expression level of BAZ1B_K426hy.

The present disclosure further provides an immunogenic polypeptide, where the polypeptide includes polypeptide A with a sequence of SKSPK-hydroxyl K-GLKTP and polypeptide B with a sequence of NSKSPK-hydroxyl K-GLKTPK. In the present disclosure, polypeptide A and polypeptide B are designed and synthesized according to a BAZ1B protein sequence and a modification type (hydroxylation modification).

Figure 1:
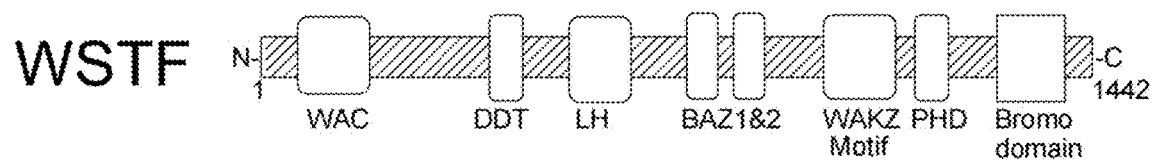
FIG. 1 shows a schematic diagram of the structure of WSTF (BAZ1B)
Figure 2:
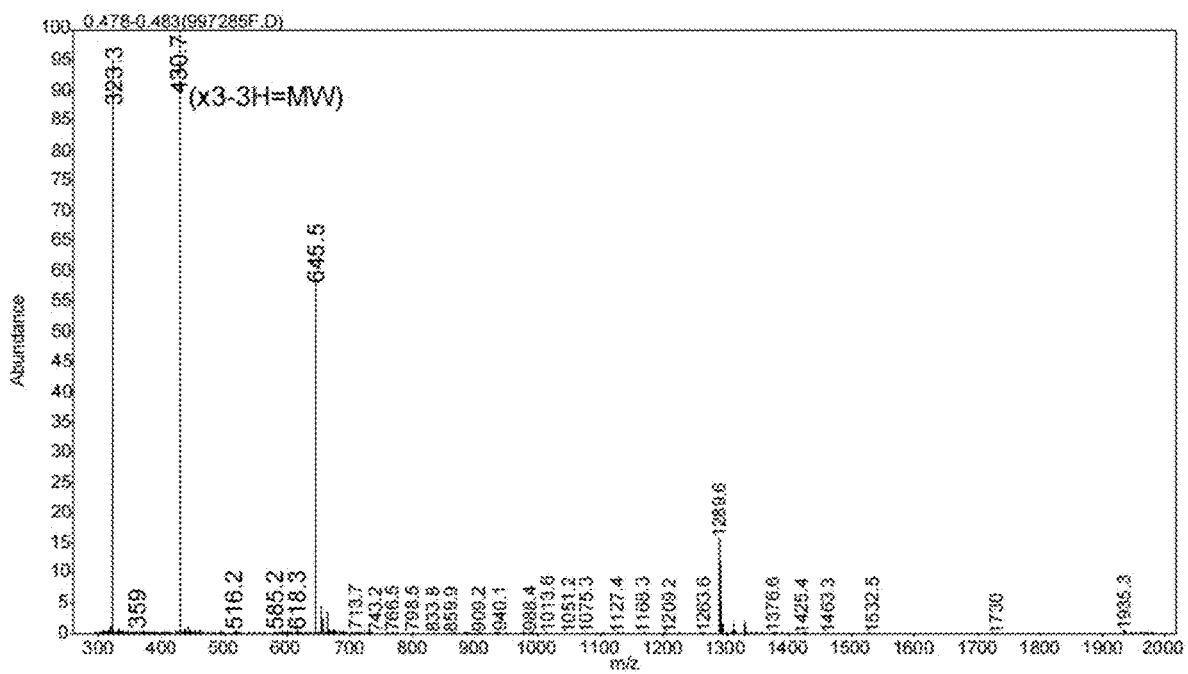
FIG. 2 shows a result of mass spectrometry detection of polypeptide A of BAZ1B.

In the present disclosure, polypeptide A has an amino acid sequence: SKSPK-(hydroxyl) K-GLKTP C (where "C" at the tail end represents a carbon terminal of the amino acid sequence), and has a molecular weight of 1289.6. The $6^{th}$-positioned "K" of the amino acid sequence is modified by hydroxylation, the amino acid has a linker sequence shown in SEQ ID NO: 1, and a mass spectrometry detection result is shown in FIG. 1. Polypeptide B has an amino acid sequence: NSKSPK-(hydroxyl) K-GLKTPK C (where "C" at the tail end represents a carbon terminal of the amino acid sequence), and has a molecular weight of 1531.8. The 7th-positioned "K" of the amino acid sequence is modified by hydroxylation, the amino acid has a linker sequence shown in SEQ ID NO: 2, and a mass spectrometry detection result is shown in FIG. 2.

The present disclosure further provides the use of the immunogenic polypeptide in the preparation of an anti-BAZ1B_K426hy polyclonal antibody. By coupling to KLH, the immunogenic polypeptide can be used for animal immunization to prepare the anti-BAZ1B_K426hy polyclonal antibody.

The present disclosure further provides an anti-BAZ1B_K426hy polyclonal antibody, where the polyclonal antibody is obtained by conducting mixed immunization on an animal with the immunogenic polypeptide. Polypeptide A and polypeptide B are separately coupled to the KLH, and a solution of coupled polypeptide A and a solution of coupled polypeptide B are mixed in a volume ratio of (1-2):(1-2) for animal immunization. The solution of coupled polypeptide A solution and the solution of coupled polypeptide B have a volume ratio of preferably 1:1, and the animal is preferably a rabbit.

The present disclosure further provides a method for preparing the polyclonal antibody, including the following steps: coupling polypeptide A and polypeptide B of the immunogenic polypeptide to the KLH separately; mixing the two solutions of coupled polypeptide according to a volume ratio of (1-2):(1-2) to conduct animal immunization; collecting a serum of an immunized animal and conducting purification to obtain the anti-BAZ1B_K426hy polyclonal antibody. Animal immunization is conducted preferably 3 to 5 times, more preferably 4 times.

As an optional embodiment, an antigen and an adjuvant are completely mixed to form a stable emulsion. The antigen mixture is drawn with a syringe and then injected subcutaneously at two points on both shoulders and two points in the muscles of both hind legs of the rabbit. About ¼ volume of the immunogen emulsion in each area can ensure the persistence of the immunogen to improve the immune response. Preferably, the antigenic polypeptide is diluted with physiological saline at a dilution ratio of 10 to 20 folds, more preferably 12 to 15 folds. The adjuvant is a Freund's adjuvant and the immunogen and the adjuvant are mixed in a ratio of 1:1.

In the present disclosure, the immunogenic polypeptide, the polyclonal antibody, or the preparation method of the polyclonal antibody can be used to prepare detection reagents for BAZ1B_K426hy protein-related diseases. Preferably, the diseases include tumors and Williams syndrome.

The technical solutions of the present disclosure will be described below clearly and completely in conjunction with the examples of the present disclosure. Apparently, the described examples are only a part of, not all of, the examples of the present disclosure. All other embodiments obtained by those of ordinary skill in the art based on the embodiments of the present disclosure without creative efforts shall fall within the protection scope of the present disclosure.

Experimental methods in the following examples are conventional methods unless otherwise specified.

The materials, reagents, and the like used in the following examples are all commercially available unless otherwise specified.

Example 1

According to the sequence and modification type of BAZ1B protein, two antigenic polypeptides were designed and synthesized, namely polypeptide A and polypeptide B, for subsequent animal immunization, purification, and detection; meanwhile, a non-modified control polypeptide (SEQ ID NO: 3, a terminal "C" represented a carbon terminal of the amino acid sequence) was designed and synthesized for purification and detection. Table 1 shows the polypeptide information.

TABLE 1

| Polypeptide information | | | |
|---|---|---|---|
| Polypeptide name | Polypeptide sequence | Modification type | Molecular weight |
| Polypeptide A | SKSPK-(hydroxyl)K-GLKTP C | Hydroxylation modification | 1289.6 |
| Polypeptide B | NSKSPK-(hydroxyl)K-GLKTPK C | Hydroxylation modification | 1531.8 |
| Control polypeptide | NSKSPKKGLKTPK C | Non-modified control | 1515.8 |

Figure 3:
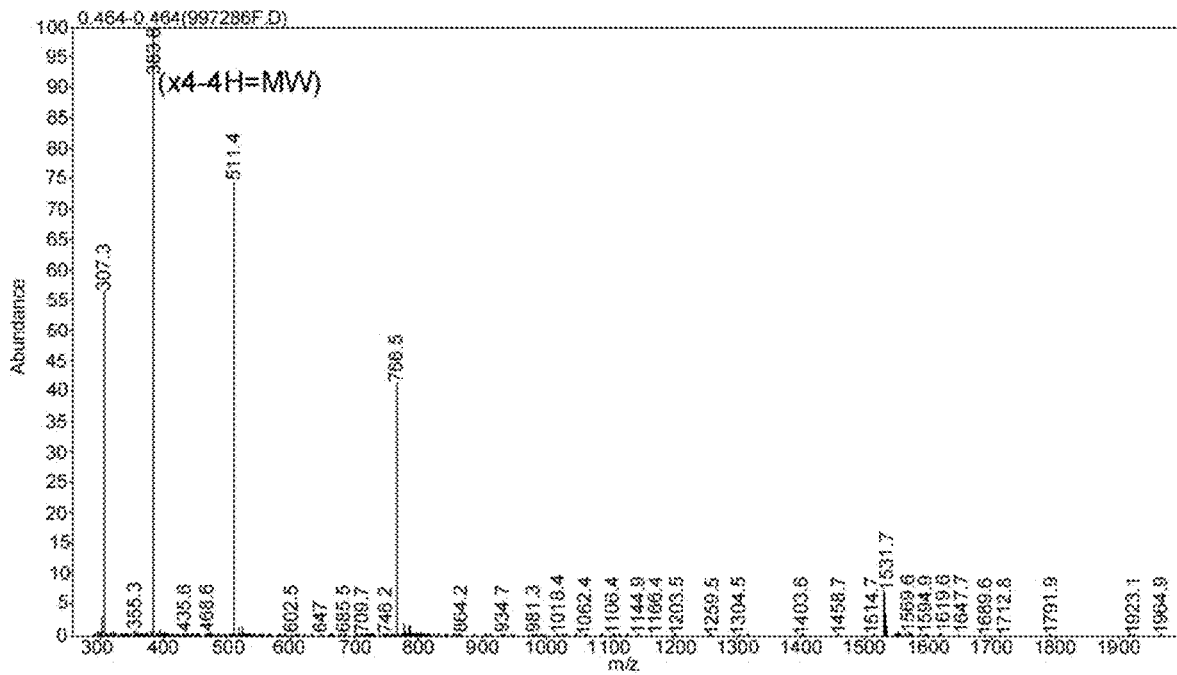
FIG. 3 shows a result of mass spectrometry detection of polypeptide B of BAZ1B.
Figure 4:
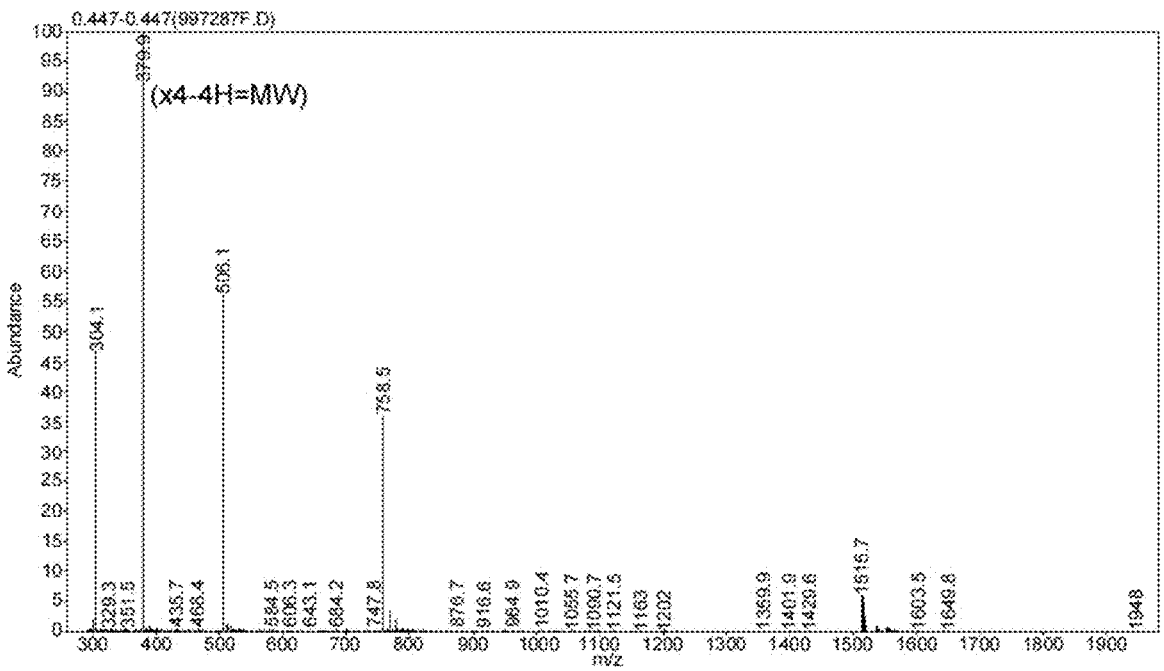
FIG. 4 shows a result of mass spectrometry detection of a non-modified polypeptide of BAZ1B.

The three sequences were detected by mass spectrometry. FIG. 2 was a mass spectrometry detection result of polypeptide A; FIG. 3 was a mass spectrometry detection result of polypeptide B; FIG. 4 was a mass spectrometry detection result of the control polypeptide. In the coordinate axes of FIG. 2 to FIG. 4, the vertical axis represented the intensity of the ion peak, and the horizontal axis represented a ratio of mass to charge. It can be seen from FIG. 2 to FIG. 4 that measured and theoretical masses of the 3 peptide fragments had a difference within 10 ppm, and the sequences were correct.

Example 2

In this example, 3 healthy New Zealand rabbits were subjected to animal immunization experiments, and the experiments were entrusted to Hangzhou PTM Biolabs Inc. to complete the immunization experiments.

1. Polypeptide Coupling

The 2 modified polypeptides (polypeptide A and polypeptide B) in Example 1 were separately coupled to KLH for rabbit immunization. The polypeptide coupling included the following steps:

(1) 20 mg of SMCC was dissolved in 2 ml of DMF.

(2) 0.8 ml of KLH was added to a 25 ml round-bottomed flask, and a 1×PBS (pH=7.2) was added to make a final protein concentration of 15 mg/ml.

(3) An obtained SMCC solution was slowly added dropwise to 120 mg of a KLH protein system, and a reaction was conducted by stirring at room temperature for 1 h.

(4) Dialysis was conducted with 1 L of a 1×PBS (pH=7.4) solution at 4° C. for 6 h to remove free SMCC.

(5) A dialyzed KLH protein was poured into a 50 ml centrifuge tube, and its volume was determined by a scale of the centrifuge tube; a protein concentration after dialysis was calculated based on an amount of the KLH protein added before the reaction, and then 2.5 mg of a KLH-SMCC solution was transferred to a 5 ml centrifuge tube according to the concentration.

(6) 3.0 mg of the polypeptide was dissolved in 0.6 ml of the 1×PBS (pH=7.2) solution.

(7) A polypeptide solution was added dropwise to the centrifuge tube with KLH-SMCC, mixed well with a vertical mixer at room temperature and reacted for 4 h.

2. Rabbit Immunization (1) Preparing Immunological Materials

The modified polypeptides coupled in step 1 were mixed at 1:1 to obtain an immunogen, the immunogen was diluted with physiological saline at a dilution ratio of 15 folds, and a diluted immunogen was mixed with a corresponding adjuvant (Freund's adjuvant) at 1:1. The antigen and the adjuvant were thoroughly mixed to form a stable emulsion, and the resulting antigen mixture was drawn with a syringe for rabbit immunization.

(2) Immunization

The antigen was injected subcutaneously at two points on both shoulders and two points in the muscles of both hind legs of the rabbit. Each area had approximately ¼ volume of the immunogen. Each rabbit was immunized for a total of 4 times on day 1, day 21, day 28, and day 35.

(3) Blood Collection

The 1st blood collection: On day 45, 30 mL of whole blood was collected and centrifuged (4,000 rpm, 5 min), and a supernatant was sent to the laboratory for serum screening and detection, including ELISA and Western blot.

The 2nd/3rd/4th blood collection: on day 50, day 65, and day, the whole blood was collected in 3 batches, with 20 mL for each time, centrifuged, and a supernatant was collected and sent to the laboratory for serum screening and detection, including ELISA and Western blot.

The rabbits subjected to mixed immunization with polypeptide A of BAZ1B and polypeptide B of BAZ1B were identified as R1, R2, and R3, respectively, and the serum ELISA results on the 45th day are shown in Table 2.

TABLE 2

Serum ELISA results

| | BAZ1B polypeptide A | | | BAZ1B polypeptide B | | | BAZ1B non-modified polypeptide | | |
|---|---|---|---|---|---|---|---|---|---|
| | R1 | R2 | R3 | R1 | R2 | R3 | R1 | R2 | R3 |
| 1:6K | 1.633 | 1.567 | 1.383 | 1.517 | 1.469 | 1.355 | 1.763 | 1.051 | 1.13 |
| 1:18K | 1.647 | 1.485 | 1.29 | 1.662 | 1.349 | 1.2 | 1.705 | 1.299 | 1.062 |
| 1:54K | 1.704 | 1.203 | 1.088 | 1.639 | 1.006 | 0.954 | 1.686 | 1.005 | 0.688 |
| 1:162K | 1.288 | 0.559 | 0.498 | 1.242 | 0.479 | 0.401 | 1.211 | 0.424 | 0.241 |
| 1:486K | 0.787 | 0.322 | 0.252 | 0.67 | 0.229 | 0.197 | 0.577 | 0.232 | 0.169 |
| 1:1458K | 0.302 | 0.142 | 0.106 | 0.253 | 0.111 | 0.085 | 0.232 | 0.112 | 0.093 |
| 1:4374K | 0.107 | 0.05 | 0.048 | 0.087 | 0.036 | 0.052 | 0.101 | 0.045 | 0.047 |
| 1:13122K | 0.107 | 0.087 | 0.096 | 0.086 | 0.082 | 0.08 | 0.1 | 0.089 | 0.086 |

According to the results of three rabbit sera detected by ELISA in Table 2, titers of the identified modified polypeptides each were above 1:10 K (OD>1).

Figure 5:
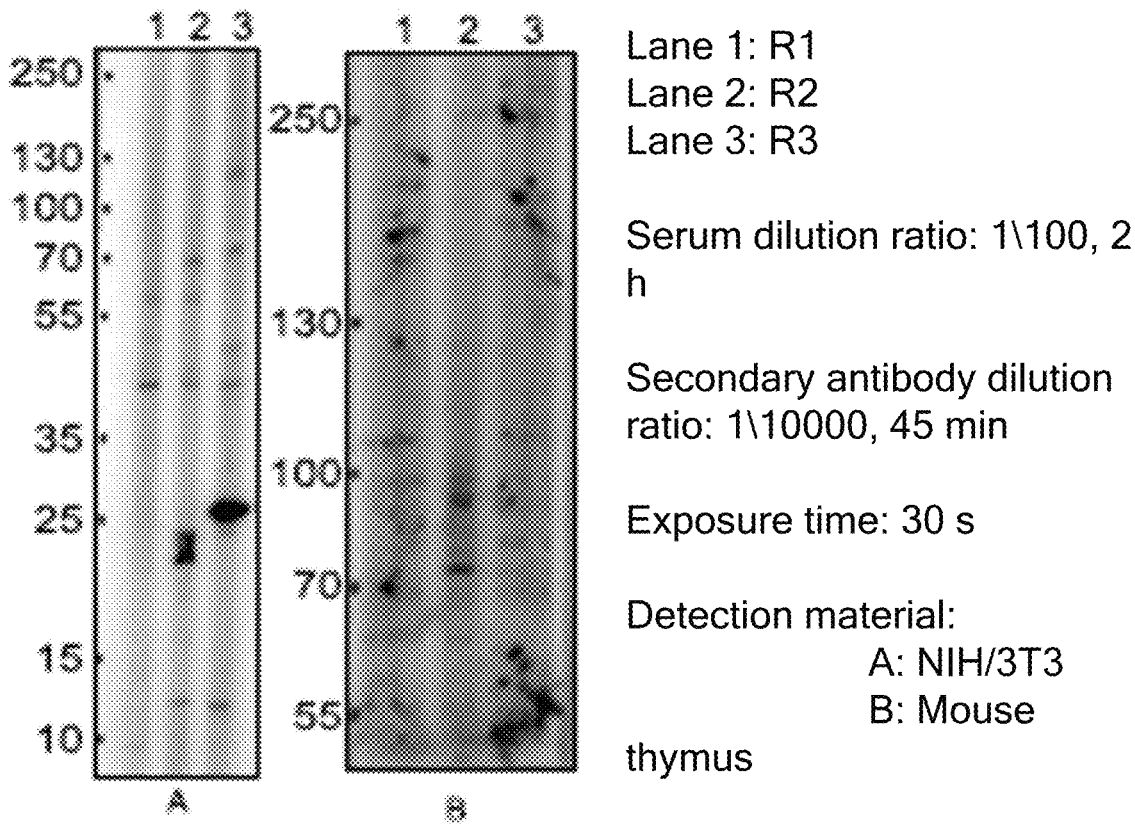
FIG. 5 shows a result of Western blot preliminary screening of a serum.

FIG. 5 showed the results of Western blot preliminary screening of the sera on the 45th day. The results of Western blot showed that the band with a theoretical molecular weight of about 175 kDa of the target protein was not detected in each serum of the three rabbits.

Based on the detection results of ELISA and Western blot, the sera of all 3 rabbits (positive test results) were selected for purification.

3. Antibody Purification (1) Preparing a Protein a Affinity Column:

10 mL of a protein A filler and an equal volume of PBS solution were mixed, stirred, and aspirated to remove air bubbles in the filler. The protein A filler was slowly added to a glass column, to cast a chromatography column. The column drying was avoided during this process.

After casting, the column was equilibrated with 10-fold volumes of a pre-chilled PBS solution.

(2) Protein a Affinity Chromatography:

After the serum was filtered with a filter, the serum sample was loaded onto the equilibrated protein A chromatography column; to test a binding efficiency of the antiserum to the filler, a loading effluent should be retained. The column was washed with a PBS solution and eluted with a 150 mM glycine buffer at a pH value of 3.4 (150 mM and pH=3.4 glycine). An eluate was collected and adjusted to a pH value of 7.0 by adding a neutralization buffer.

(3) Enriching a Target Antibody:

The crude IgG obtained after purification of protein A was loaded onto an equilibrated antigen polypeptide affinity chromatography column to specifically enrich the target antibody.

(4) Removal of Non-Specific Antibodies:

The target antibody in the previous step was loaded onto a non-modified affinity chromatography column, and an effluent (FT3) was directly collected to remove non-specific antibody components. An anti-BAZ1B_K426hy polyclonal antibody was obtained.

(5) Preservation of the Antibody:

Protein content was determined. The antibody was stored in 10% glycerol, and a purified antibody was aliquoted and stored at −20° C. The purified antibodies from R1 to R3 were labeled as Ab1 to Ab3, respectively.

Example 3

ELISA, Dot blot, and Western blot were conducted on the purified anti-BAZ1B_K426hy polyclonal antibodies Ab1, Ab2, and Ab3 prepared in Example 2, respectively.

1. ELISA Detection (1) Antigen Coating:

The antigen (antigen-modified polypeptide) was diluted 10-fold with a coating solution (PBS), added at 50 μg/well into an ELISA plate in sequence, and stored in a refrigerator at 4° C. overnight.

(2) Washing the Plate:

The ELISA plate coated on the previous day was added with a washing solution 1×TBST for washing 3 times in total by filling the wells of the plate.

(3) Blocking:

A 1% BSA blocking solution was added to the washed ELISA plate, where each reaction well was filled with the blocking solution, incubated at 37° C. for 1 h, and then added with the washing solution 1×TBST for washing 2 times in total by filling wells of the plate.

(4) Incubation of a Primary Antibody:

The antibody was serially diluted according to 1:1 K, and the concentrations after dilution were shown in Table 3. The obtained antibody diluents were added to the ELISA plate in sequence at 100 μL per well, incubated at 37° C. for 1.5 h, and then added with the washing solution 1×TBST for washing for 2 times in total by filling wells of the plate.

(5) Incubation of a Secondary Antibody:

The secondary antibody (rabbit antibody) was diluted to 1:10 K with 100 μL of a 1% BSA blocking solution, incubated at 37° C. for 45 min, and then added with the washing solution 1×TBST for washing for 2 times in total by filling wells of the plate.

(6) Color Development:

100 μL of a TMB chromogenic solution was added, and 8 min later, 100 μL of 1 M sulfuric acid was added to terminate the color development, and the data was read with a microplate reader. The ELISA detection results of the antibodies were shown in Table 3.

TABLE 3

ELISA detection results of antibodies

| | Ab1 | | | Ab2 | | | Ab3 | | |
|---|---|---|---|---|---|---|---|---|---|
| | Polypeptide A | Polypeptide B | Non-modified polypeptide | Polypeptide A | Polypeptide B | Non-modified polypeptide | Polypeptide A | Polypeptide B | Non-modified polypeptide |
| 1:600 | 2.147 | 2.126 | 2.069 | 2.065 | 1.936 | 1.941 | 2.035 | 2.035 | 1.75 |
| 1:1800 | 2.107 | 1.894 | 1.802 | 2.015 | 1.868 | 1.695 | 1.943 | 1.782 | 1.339 |
| 1:5400 | 2.127 | 1.556 | 1.373 | 1.765 | 1.909 | 1.635 | 1.656 | 1.001 | 0.645 |
| 1:16200 | 1.697 | 1.111 | 0.696 | 1.55 | 1.541 | 1.267 | 1.172 | 0.463 | 0.334 |
| 1:48600 | 1.313 | 0.636 | 0.375 | 1.119 | 1.052 | 0.684 | 0.722 | 0.29 | 0.209 |
| 1:145800 | 0.696 | 0.242 | 0.148 | 0.544 | 0.488 | 0.352 | 0.275 | 0.135 | 0.209 |
| 1:437400 | 0.272 | 0.085 | 0.054 | 0.217 | 0.199 | 0.115 | 0.111 | 0.067 | 0.032 |
| 1:1312200 | 0.138 | 0.072 | 0.072 | 0.136 | 0.121 | 0.103 | 0.08 | 0.071 | 0.052 |

The ELISA detection results in Table 3 showed that the ability of three antibodies to recognize at least one modified polypeptide was not less than 1:50 K dilution; where hybridization signals of Ab1 and Ab3 for recognizing the modified polypeptides were 10 times stronger than that for recognizing the non-modified polypeptides.

2. Dot Blot Detection (1) Spotting:

Uncrosslinked antigenic polypeptide A, antigenic polypeptide A, and non-modified polypeptide were spotted onto a PVDF membrane separately according to a gradient of 1 ng, 4 ng, 16 ng, and 64 ng.

(2) Blocking:

After the membrane surface was dry, a blocking solution (3 ml to 5 ml of 500 nonfat milk) was added for blocking at room temperature for 60 min.

(3) Washing:

The membrane was washed with 1×TBST for 10 min.

(4) Incubation of a Primary Antibody:

The antibody was diluted to a concentration of 1:2000 with 5% nonfat dry milk, incubated at room temperature for 2 h, and washed 3 times with the 1×TBST for 8 min in each time.

(5) Incubation of a Secondary Antibody:

A rabbit antibody was selected as the secondary antibody; the secondary antibody was added at a dilution ratio of 1:10 K, incubated at room temperature for 1 h, and then washed 3 times with the 1×TBST for 8 min each time.

(6) 0.5 ml to 1 ml of a chromogenic solution (Chemiluminescent HRP Substrate) was added to the washed membrane for exposure.

Figure 6:
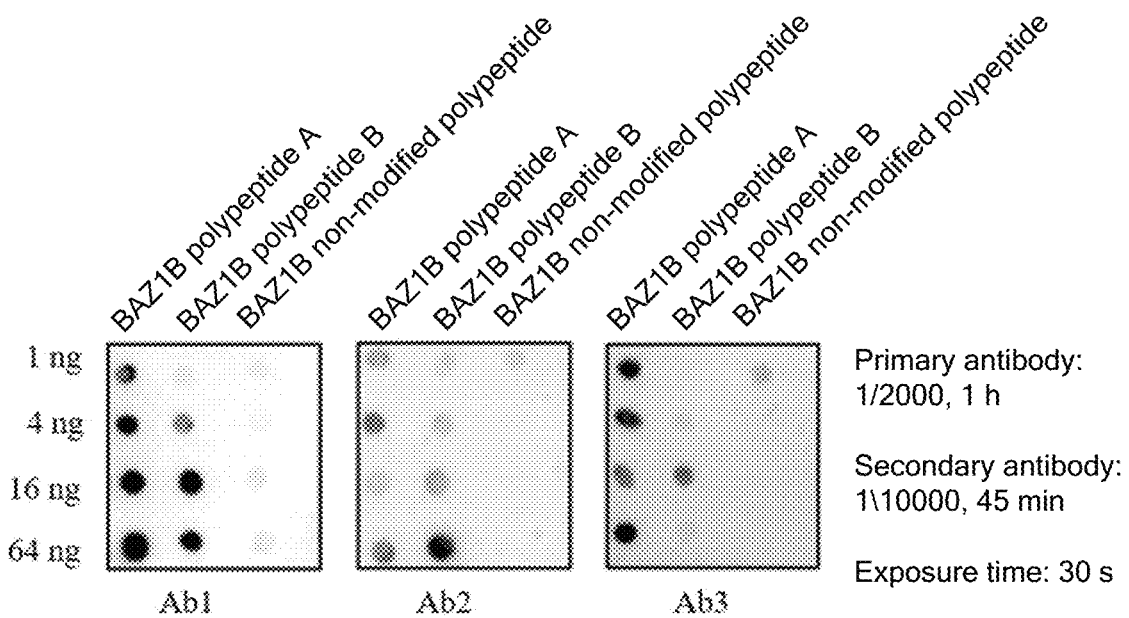
FIG. 6 shows a result of Dot blot detection of an antibody.

The Dot blot detection results of the antibodies were shown in FIG. 6. It was seen from FIG. 6 that the Ab1, Ab2, and Ab3 did not bind to negative non-modified polypeptides, but had strong binding to positively modified polypeptides, especially polypeptide A.

3. Western Blot Detection (1) Lysis of Cells:

According to experimental demands, cells or tissues were selected for detection; according to different samples, different cleavage methods were selected to obtain a whole protein of the sample, and a protein concentration was determined by a BCA method:

Heating a 1×Hot lysis buffer: the 1×Hot lysis buffer was heated in a water bath to nearly 100° C.

Cells: 3 ml of a boiled 1×Hot lysis buffer was added per 1 ml volume of cells (estimated amount of cell pellets), and the cells were blown off with a pipette; the cells were boiled in a water bath, and then pipetted back and forth with the pipette until obtaining a transparent, clear, and homogeneous liquid. Tissues: an appropriate amount of tissues were cut into pieces with scissors, pipetted with an appropriate amount of the 1×Hot lysis buffer, and boiled in a water bath for at least 20 min with pipetting every 5 min.

Tips: a ratio of the tissues to the 1×Hot lysis buffer was adjusted according to a protein yield (for tissues with lower protein content, the amount of lysis buffer was reduced).

Eyeball, pituitary, hippocampus, and the like with a lower yield were added at a volume ratio of 1:2, while other tissues with a high yield were added at a volume ratio of 1:3.

Sonication: at 25% W for 5 min, 3 sec of each sonication with 5 sec of interval.

Tips: during the sonication, the sample must be placed in an ice-water mixture, a probe must be below the liquid level, and the sonication time should be less than the interval time to avoid bubbles. Each time a new cell or tissue was lysed, the probe should be ultrasonically washed with pure water for 3 sec, and then gently wiped to dryness with lint-free paper to avoid cross-contamination.

A preparation method of the 1×Hot Lysis buffer (100 ml) included: 1 g of SDS (1% w/v), 0.12 g of Tris-base (10 mM) g, and 18 mg of sodium orthovanada (1.0 mM) was added to 80 ml of deionized water and dissolve completely, adjusted to a pH value of 8.0 with HCl, and diluted to 100 ml.

(2) Protein Electrophoresis and Transfer:

Protein electrophoresis: a 6% separation gel was selected. 10% ammonium persulfate and TEMED were added at the end of the gel preparation, and 4.7 mL of the separation gel was added per plate. 20 μg of the sample per well was loaded and subjected to electrophoresis; electrophoresis conditions were: stacking gel 80 V and separation gel 120 V.

Wet transfer: a transfer liquid was pre-cooled before transfer and the gel, membrane, and filter paper were spread in the transfer liquid to form a sandwich structure to avoid air bubbles. A transfer voltage was 120 V.

(3) Blocking:

The transferred membrane was blocked with a blocking solution (5% nonfat dry milk) for 60 min at room temperature. After incubation, the membrane was washed with the 1×TBST for 10 min.

(4) Incubation of a Primary Antibody:

The antibody was diluted with 5% nonfat dry milk (1:100/1:500), incubated at room temperature for 2 h, and washed 3 times with the 1×TBST for 8 min each time.

(5) Incubation of a Secondary Antibody:

A rabbit antibody was selected as the secondary antibody; the secondary antibody was added at a dilution ratio of 1:10 K, incubated at room temperature for 1 h, and then washed 3 times with the 1×TBST for 8 min each time.

(6) A Chromogenic Substrate was Added to a Washed Membrane for Exposure.

Figure 7:
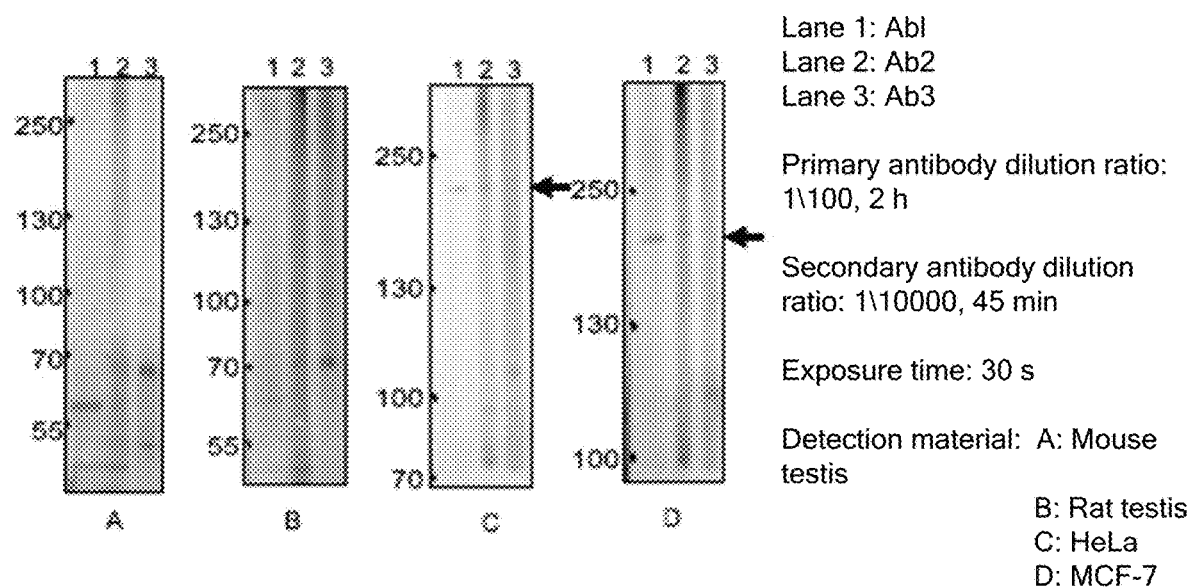
FIG. 7 shows the results of Western blot detection of the antibody, where A to D represent cell lysates of Mouse testis, Rat testis, HeLa, and MCF-7, respectively.

The Western blot detection results of the antibodies were shown in FIG. 7, and the target bands of the antibodies Ab1 and Ab2 of about 175 KDa were detected in the HeLa and MCF-7 cell lysates.

Figure 8:
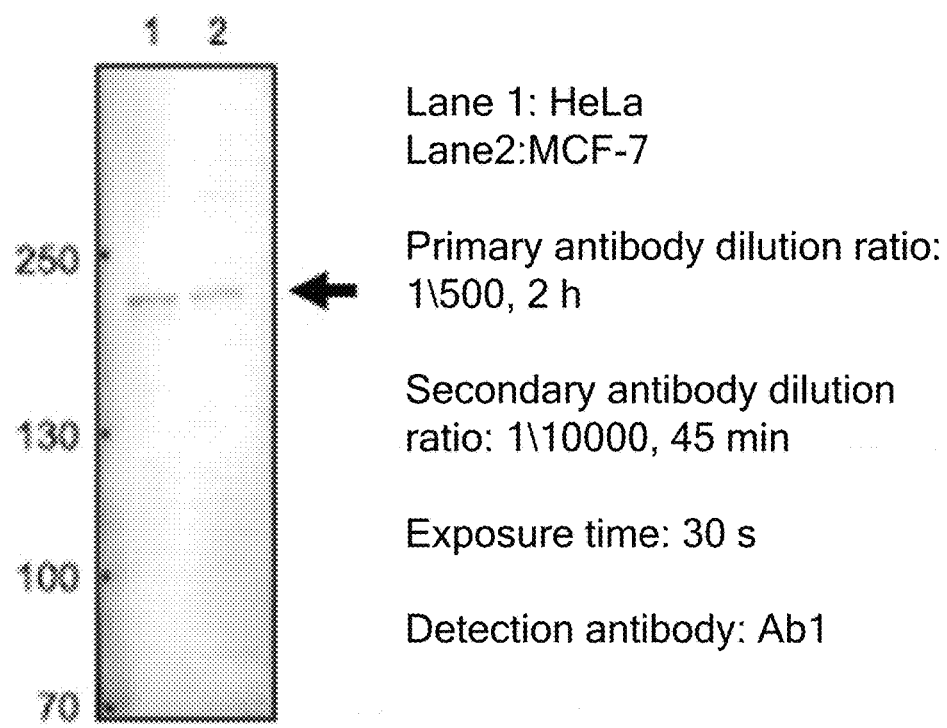
FIG. 8 shows the results of Western blot detection of Ab1 in the HeLa and MCF-7 lysates.

Ab1 was confirmed by another Western blot experiment in HeLa and MCF-7 cell lysates, and the results were shown in FIG. 8. According to the Western blot results in FIG. 8, the target band of Ab1 was detected in the HeLa and MCF-7 cell lysates. The positive detection limit of Dot blot reached 4 ng and was 10 times stronger than the recognition of non-modified polypeptides. The results of Western blot experiments showed that the antibody Ab1 could specifically recognize the endogenous protein BAZ1B_K426hy.

Example 4

1. Cell Cultivation

MCF-7 cells (non-triple-negative breast cancer cells): the cells were incubated in a DMEM medium containing 10% FBS and 1% double antibody at 37° C. in a cell incubator containing κ% $CO_2$.

2. Cell Transfection (1) Cell Grouping

Experimental group 1: WSTF+si-NC, WSTF expression and non-specific siRNA control group;

Experimental group 2: WSTF+si-JMJD6, WSTF expression and JMJD6-specific siRNA experimental group;

Experimental group 3: WSTF+JMJD6 WT, WSTF expression and wild-type JMJD6 control group;

Experimental group 4: WSTF+JMJD6 Mut, WSTF expression and mutant JMJD6 experimental group;

Experimental group 5: MCF-7/WSTF$^{-/-}$+si-NC, low WSTF expression and non-specific siRNA control group;

Experimental group 6: MCF-7/WSTF$^{-/-}$+si-JMJD6, low WSTF expression and JMJD6-specific siRNA experimental group;

Experimental group 7: MCF-7/WSTF$^{-/-}$+JMJD6 WT, low WSTF expression and wild-type JMJD6 control group;

Experimental group 8: MCF-7/WSTF$^{-/-}$+JMJD6 Mut, low WSTF expression and mutant JMJD6 experimental group.

(2) Cell inoculation: MCF-7 or MCF-7/WSTF$^{-/-}$ cells in a logarithmic growth phase (a cell line with knockdown of WSTF) were inoculated in a 6-well plate, and a cell density was about 60% to 70% at the time of transfection the next day.

(3) Preparation of transfection solutions: transfection solutions A and B were prepared in 1.5 mL sterile centrifuge tubes separately.

Preparation of the Transfection Solution A:

Experimental group 1, transfection solution A: 0.5 µg of WSTF was diluted with a serum-free medium Opti-MEM, and 0.5 µL of si-NC was added to the serum-free medium Opti-MEM to a final volume of 50 µL, and then mixed gently;

Experimental group 2, transfection solution A: 0.5 µg of WSTF was diluted with a serum-free medium Opti-MEM, and 0.5 µL of si-JMJD6 was added to the serum-free medium Opti-MEM to a final volume of 50 µL, and then mixed gently;

Experimental group 3, transfection solution A: 0.5 µg of WSTF was diluted with a serum-free medium Opti-MEM, and 0.5 µL of JMJD6 WT was added to the serum-free medium Opti-MEM to a final volume of 50 µL, and then mixed gently;

Experimental group 4, transfection solution A: 0.5 µg of WSTF was diluted with a serum-free medium Opti-MEM, and 0.5 µL of JMJD6 Mut was added to the serum-free medium Opti-MEM to a final volume of 50 µL, and then mixed gently;

Experimental group 5, transfection solution A: 0.5 µg of MCF-7/WSTF$^{-/-}$ was diluted with a serum-free medium Opti-MEM, and 0.5 µL of si-NC was added to the serum-free medium Opti-MEM to a final volume of 50 µL, and then mixed gently;

Experimental group 6, transfection solution A: 0.5 µg of MCF-7/WSTF$^{-/-}$ was diluted with a serum-free medium Opti-MEM, and 0.5 µL of si-JMJD6 was added to the serum-free medium Opti-MEM to a final volume of 50 µL, and then mixed gently;

Experimental group 7, transfection solution A: 0.5 µg of MCF-7/WSTF$^{-/-}$ was diluted with a serum-free medium Opti-MEM, and 0.5 µL of JMJD6 WT was added to the serum-free medium Opti-MEM to a final volume of 50 µL, and then mixed gently;

Experimental group 8, transfection solution A: 0.5 µg of MCF-7/WSTF$^{-/-}$ was diluted with a serum-free medium Opti-MEM, and 0.5 µL of JMJD6 Mut was added to the serum-free medium Opti-MEM to a final volume of 50 µL, and then mixed gently;

Preparation of the transfection solution B: 1 µL of Lipofectamine 2000 was gently mixed before use, and then added to the serum-free medium Opti-MEM to a final volume of 50 µL, mixed gently, and then incubated at room temperature for 5 min.

The transfection solution B was added to the transfection solution A of each experimental group, mixed well by flicking, and incubated at room temperature for 20 min by standing.

Each of obtained mixed solutions was slowly and evenly added dropwise to the culture flask, mixed well, incubated at 37° C. for 5 h in a 5% $CO_2$ incubator, and then transferred to a normal medium to continue incubation.

3. Transwell Detection of Invasive Ability of Cells in Each Group (1) The cell medium of each group was thoroughly discarded, the cells were washed once with PBS and subjected to digestion by adding a digestion solution (0.02% EDTA and 0.25% trypsin) to each well; the cells were added with a DMEM medium containing 10% FBS to terminate the digestion, and then mixed well by pipetting to conduct the Transwell experiment.

(2) A bottom surface of each Transwell chamber was coated with 10 µL of fibronectin (0.5 mg/mL) and air-dried in an ultra-clean bench to solidify the fibronectin on the bottom surface of the membrane.

(3) 50 µL of a matrix gel was dissolved and added to each well, and the cells in each group were digested and counted; $10^5$ cells were placed in a 1.5 mL EP tube, centrifuged at 2,000 rpm for 5 min, a supernatant was removed, the cells were resuspended with 200 µL of a serum-free DMEM medium, and then added to the Transwell chamber. A DMEM medium containing 20% Gibico serum was added to the lower chamber. The chamber was incubated in a 37° C. incubator for 24 h.

(4) The Transwell chamber was taken out, the cells inside were wiped with a cotton swab, and the remaining cells were gently washed off with PBS. Cells on the reverse side of the Transwell chamber were fixated with a mixture of methanol and glacial acetic acid at 3:1 for 30 min. The cells were stained in a crystal violet staining solution for 15 min. The membrane was washed and mounted on a glass slide for observation.

(5) Under the microscope, 3 random fields of view were selected to take pictures, and a histogram was drawn for analysis. The results were shown in FIG. 9.

Figure 9:
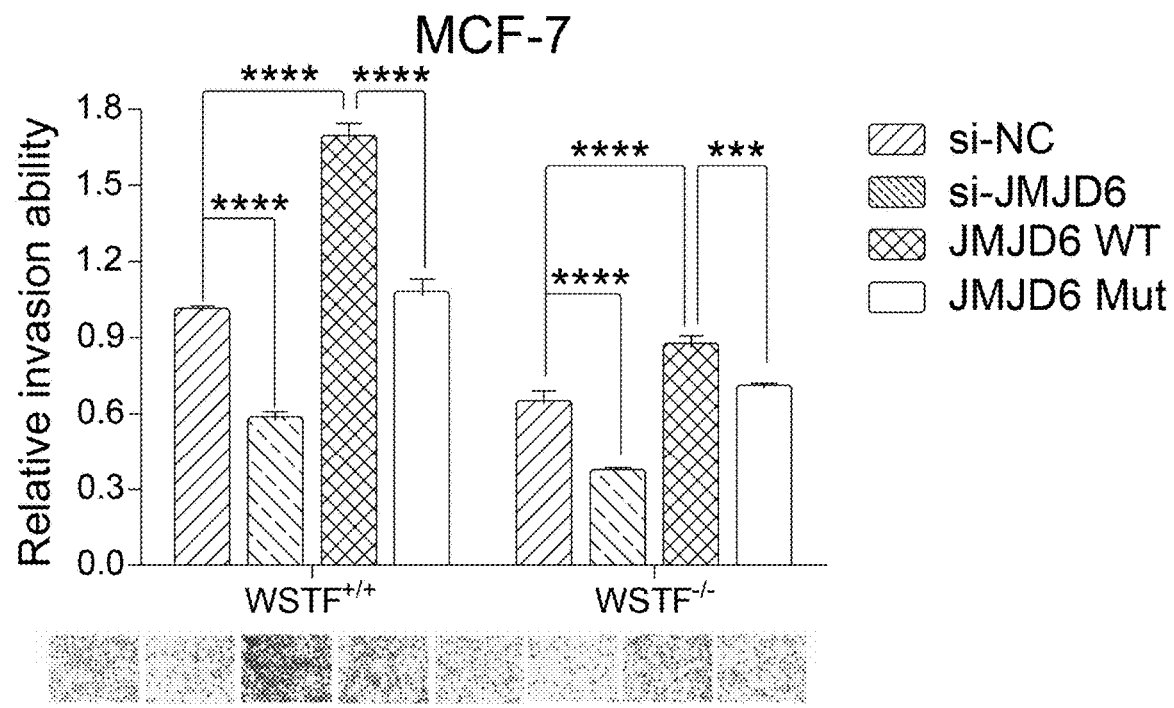
FIG. 9 shows the results of Transwell detection of invasive ability of cells in each group.

It was seen from FIG. 9 that the JMJD6-WSTF$^{K426hy}$ axis had the ability to regulate cell invasion.

4. Clone Formation Assay in Detecting the Clone Formation Ability of Each Group of Cells (1) The cell medium of each group was thoroughly discarded, the cells were washed once with PBS and subjected to digestion by adding a digestion solution (0.02% EDTA and 0.25% trypsin) to each well; the cells were added with a DMEM medium containing 10% FBS to terminate the digestion, and then mixed well by pipetting to conduct the clone formation experiment.

(2) The cells were counted in each group, and 300 cells were inoculated in a 12-well plate and supplemented with a complete medium to 2 mL. The cells were incubated at 37° C. in a 5% $CO_2$ incubator for 1 to 2 weeks.

(3) When the number of cells in each clone grew to more than 50, the complete medium was discarded, and the cells were washed with PBS once; 500 μL of 4% paraformaldehyde was added to each well to fixate the cells at 4° C. for 30 min; the cells were washed with PBS once, and stained by 500 μL of 0.1% crystal violet in each well, and rinsed with water.

(5) After the culture plate was dried, the cells were photographed by a camera and a histogram was drawn for analysis. The results were shown in FIG. 10.

Figure 10:
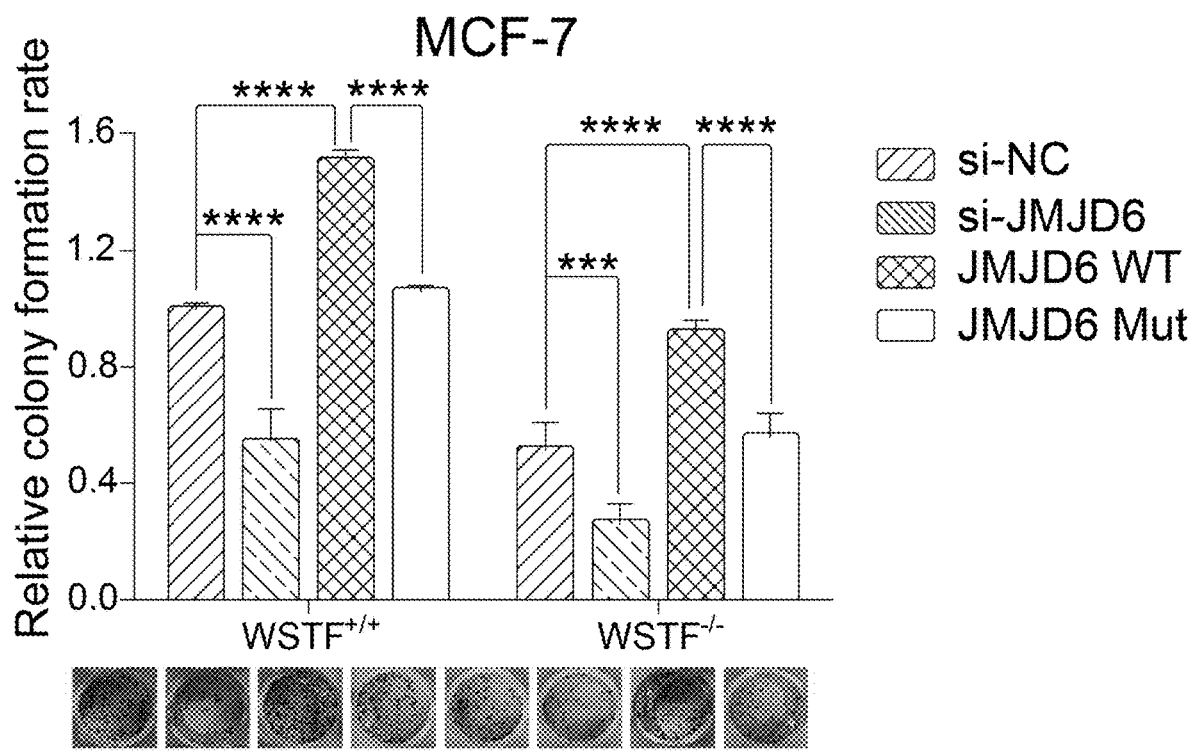
FIG. 10 shows the proliferation ability of each group of cells detected by a clone formation assay.

It was seen from FIG. 10 that the JMJD6-WSTF$^{K426hy}$ axis had the ability to regulate cell clone formation.

Example 5

The expression level of hydroxylated WSTF (BAZ1B) was detected by the purified anti-BAZ1B_K426hy polyclonal antibody Ab1 prepared in Example 2.

1. Cell Cultivation

MCF-7 cells: the cells were incubated in a DMEM medium containing 10% FBS and 1% double antibody at 37° C. in a cell incubator containing 5% $CO_2$.

2. Cell Transfection (1) Cell Grouping

Experimental group 1: WSTF+si-NC, WSTF expression and non-specific siRNA control group;

Experimental group 2: WSTF+si-JMJD6, WSTF expression and JMJD6-specific siRNA experimental group;

Experimental group 3: WSTF+JMJD6 WT, WSTF expression and wild-type JMJD6 control group;

Experimental group 4: WSTF+JMJD6 Mut, WSTF expression and mutant JMJD6 experimental group;

Experimental group 5: MCF-7/WSTF$^{-/-}$+si-NC, low WSTF expression and non-specific siRNA control group;

Experimental group 6: MCF-7/WSTF$^{-/-}$+si-JMJD6, low WSTF expression and JMJD6-specific siRNA experimental group;

Experimental group 7: MCF-7/WSTF$^{-/-}$+JMJD6 WT, low WSTF expression and wild-type JMJD6 control group;

Experimental group 8: MCF-7/WSTF$^{-/-}$+JMJD6 Mut, low WSTF expression and mutant JMJD6 experimental group.

(2) Cell inoculation: MCF-7 or MCF-7/WSTF$^{-/-}$ cells in a logarithmic growth phase (a cell line with knockdown of WSTF) were inoculated in a 6-well plate, and a cell density was about 60% to 70% at the time of transfection the next day.

(3) Preparation of transfection solutions: transfection solutions A and B were prepared in 1.5 mL sterile centrifuge tubes separately.

Preparation of the Transfection Solution A:

Experimental group 1, transfection solution A: 1.5 μg of WSTF was diluted with a serum-free medium Opti-MEM, and 1.5 μL of si-NC was added to the serum-free medium Opti-MEM to a final volume of 50 μL, and then mixed gently;

Experimental group 2, transfection solution A: 1.5 μg of WSTF was diluted with a serum-free medium Opti-MEM, and 1.5 μL of si-JMJD6 was added to the serum-free medium Opti-MEM to a final volume of 50 μL, and then mixed gently;

Experimental group 3, transfection solution A: 1.5 μg of WSTF was diluted with a serum-free medium Opti-MEM, and 1.5 μL of JMJD6 WT was added to the serum-free medium Opti-MEM to a final volume of 50 μL, and then mixed gently;

Experimental group 4, transfection solution A: 1.5 μg of WSTF was diluted with a serum-free medium Opti-MEM, and 1.5 μL of JMJD6 Mut was added to the serum-free medium Opti-MEM to a final volume of 50 μL, and then mixed gently;

Experimental group 5, transfection solution A: 1.5 μg of MCF-7/WSTF$^{-/-}$ was diluted with a serum-free medium Opti-MEM, and 1.5 μL of si-NC was added to the serum-free medium Opti-MEM to a final volume of 50 μL, and then mixed gently;

Experimental group 6, transfection solution A: 1.5 μg of MCF-7/WSTF$^{-/-}$ was diluted with a serum-free medium Opti-MEM, and 1.5 μL of si-JMJD6 was added to the serum-free medium Opti-MEM to a final volume of 50 μL, and then mixed gently;

Experimental group 7, transfection solution A: 1.5 μg of MCF-7/WSTF$^{-/-}$ was diluted with a serum-free medium Opti-MEM, and 1.5 μL of JMJD6 WT was added to the serum-free medium Opti-MEM to a final volume of 50 μL, and then mixed gently;

Experimental group 8, transfection solution A: 1.5 μg of MCF-7/WSTF$^{-/-}$ was diluted with a serum-free medium Opti-MEM, and 1.5 μL of JMJD6 Mut was added to the serum-free medium Opti-MEM to a final volume of 50 μL, and then mixed gently;

Preparation of the transfection solution B: 3 μL of a Lipofectamine2000 Reagent was diluted with the serum-free medium Opti-MEM to a final volume of 50 μL, mixed gently, and allowed to stand at room temperature for 5 min.

The transfection solution B was added dropwise to the transfection solution A of each experimental group, mixed well by flicking, and allowed to stand at room temperature for 20 min.

(4) Transfection: the transfection solution was added to the corresponding wells at 100 L/well, 600 μL of the Opti-MEM was added to each well and then evenly distributed by shaking the culture plate gently, and incubated at 37° C. in a 5% $CO_2$ cell incubator.

After 4 h, each well was replaced with 3 mL of a complete medium of 10% FBS (without antibiotics) and then continued to incubate at 37° C. in a cell incubator with 5% $CO_2$.

3. WB Detection of an Expression Level of Hydroxylated WSTF (1) Lysis of cell nuclei: after 48 h, the original culture solution of transfected cells in each experimental group was aspirated and discarded (in the 6-well plate), washed once with 1×PBS, and 1 mL of 0.05% trypsin was added to digest the cells, the cells were pipetted with 1 mL of a complete medium and collected into a 1.5 mL EP tube, centrifuged at 2,000 rpm for 5 min, resuspended in PBS and rinsed once; after a supernatant was completely discarded, 150 μL of 0.4% NP-40 (containing protease inhibitor cocktail) was added, vortexed for 5 min, and centrifuged at 5,000 rpm at 4° C. for 10 min, the obtained pellets were the nucleus; 100 μL of 0.1% NP-40 (containing protease inhibitor cocktail) was added to the pellets, mixed by flicking, centrifuged at 5,000 rpm at 4° C. for 10 min, the supernatant was discarded completely, 100 μL of RIPA was added, mixed well and dispersed, and nucleoproteins were obtained by freezing and thawing once at −80° C.

(2) A SDS denaturing 6% polyacrylamide gel was prepared (lower separation gel, single-sided).

TABLE 4

| Formulation of 6% polyacrylamide gel | |
|---|---|
| Component | Volume |
| DDW | 5.8 mL |
| 40% acrylamide | 1.5 mL |
| 1.5M Tris-Cl (pH = 8.8) | 2.5 mL |
| 10% SDS | 100 μL |
| 10% ammonium persulfate | 100 μL |
| TEMED | 4.0 μL |

Ater mixing, the gel was quickly poured to about ⅔ of the total height of the glass plate, and then 1 mL of water-saturated n-butanol was added on the top of the gel to ensure the smoothness of the upper layer of the gel, and allowed to stand for the gel to solidify.

(3) A SDS denaturing 5% polyacrylamide gel was prepared (upper stacking gel, single-sided)

TABLE 5

| Formulation of 5% polyacrylamide gel | |
|---|---|
| Component | Volume |
| DDW | 2.225 mL |
| 40% acrylamide | 375 μL |
| 1.5M Tris-Cl (pH = 6.8) | 380 μL |
| 10% SDS | 30 μL |
| 10% ammonium persulfate | 30 μL |
| TEMED | 3.0 μL | ter mixing, the gel was quickly poured until the glass plate was filled, the comb was inserted, and allowed to stand for the gel to solidify. Before electrophoresis, the comb was removed, the gel was placed in a 1×Tris-glycine running buffer, and the sample wells were blown out with a syringe needle.

(4) The protein sample was mixed with a 5× loading buffer (containing β-mercaptoethanol), boiled for 5 min to denature, and then treated in an ice bath for 5 min. An appropriate amount of protein sample was loaded and subjected to SDS denaturing 6% polyacrylamide gel electrophoresis until the target protein was effectively separated and the electrophoresis was terminated.

(5) After electrophoresis, the gel was taken out and placed in a special sandwich clip for transfer, the gel was placed in the negative electrode, the PVDF membrane was placed in the positive electrode, and the membrane was transferred at a constant current of 350 mA in a transfer buffer for 2 h at 4° C., such that proteins in the gel were transferred to PVDF membranes to form blots.

(6) The membrane was put in 1×Blotto, and shaken at room temperature for 2 h.

(7) The membrane was cut according to a blotting position of the protein, placed in Blotto containing the corresponding primary antibody (purified polyclonal antibody Ab1 prepared in Example 2), and shaken at 4° C. overnight.

(8) The membrane was placed in the 1×TBST, shaken, and rinsed for 5 min, a total of 4 times.

(9) The membrane was placed in Blotto containing the corresponding secondary antibody (HRP-labeled goat anti-rabbit IgG antibody) for 1.5 h at room temperature.

(10) The membrane was placed in the 1×TBST, shaken, and rinsed for 5 min, a total of 4 times.

(11) The membrane was placed in Western Lightning™ Chemiluminescence Reagent for 30 sec.

(12) The membrane was immediately placed in an exposure box, and a photosensitive film was exposed for 1 min in a dark room, and then developed and fixated.

(13) The film was photographed with a LabWorks™ gel imaging and analysis system, and the brightness values of bands of each group were analyzed. The method included: a ratio of a target band brightness value of each sample to a band brightness value of the corresponding LMNB1 (internal reference) was calculated to obtain a corrected target band brightness value. Taking the control group as a standard value 1, and a histogram was drawn, the results were shown in FIG. 11.

Figure 11:
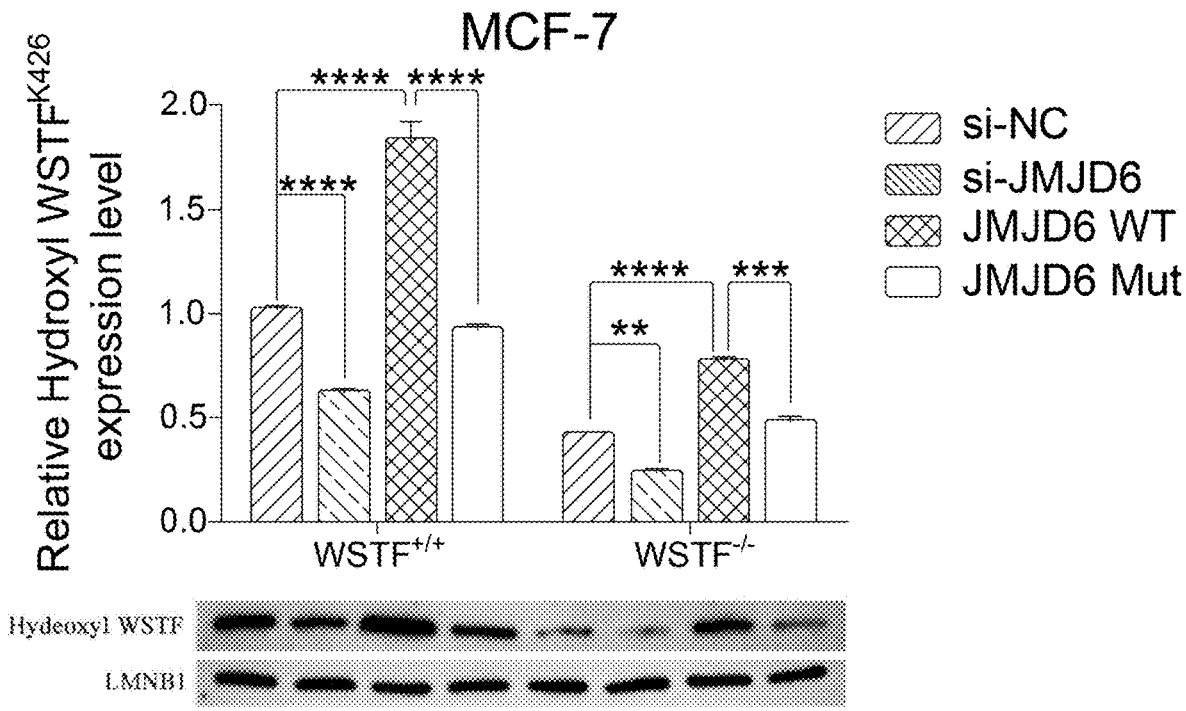
FIG. 11 shows the results of WB detection on expression levels of BAZ1B_K426hy in MCF-7 cells with knockdown, overexpression, or mutant of JMJD6.

It was seen from FIG. 11 that after JMJD6 knockdown or mutation, the level of WSTF hydroxylation was significantly reduced.

The results of Examples 4 to 5 showed that Lys426 hydroxylation (K426hy) could inhibit the transcriptional regulatory activity of WSTF and induce its degradation. In breast cancer cells, JMJD6 could negatively regulate the transcription factor activity and self-stability of WSTF through hydroxylation, thereby affecting the occurrence and development of tumors.

Example 6

The expression level of hydroxylated WSTF (BAZ1B) in different cells was detected by the purified anti-BAZ1B_K426hy polyclonal antibody Ab1 prepared in Example 2.

1. Cell Cultivation

Beas-2B (human normal lung epithelial cells): the cells were incubated in a DMEM medium containing 10% FBS and 1% double antibody at 37° C. in a cell incubator containing 5% $CO_2$;

A549 (human lung cancer cells): the cells were incubated in a medium containing 10% FBS and 1% double antibody Ham's F-12K at 37° C. in a cell incubator containing 5% $CO_2$;

MDA-MB-231 (human triple-negative breast cancer cells): the cells were incubated in a DMEM medium containing 10% FBS and 1% double antibody at 37° C. in a cell incubator containing 5% $CO_2$;

SW620 (human colorectal cancer cells): the cells were incubated in a DMEM medium containing 10% FBS and 1% double antibody at 37° C. in a cell incubator containing 5% $CO_2$;

A375 (human melanoma cells): the cells were incubated in a DMEM medium containing 10% FBS and 1% double antibody at 37° C. in a cell incubator containing 5% $CO_2$;

MGC-803 (human gastric cancer cells): the cells were incubated in a 1640 medium containing 10% FBS and 1% double antibody at 37° C. in a cell incubator containing 5% $CO_2$;

HeLa (human cervical cancer cells): the cells were incubated in a 1640 medium containing 10% FBS and 1% double antibody at 37° C. in a cell incubator containing 5% $CO_2$;

U251 (human glioma cells): the cells were incubated in a DMEM/F12 medium containing 10% FBS and 1% double antibody at 37° C. in a cell incubator containing 5% $CO_2$;

Eca-109 (human esophageal cancer cells): the cells were incubated in a 1640 medium containing 10% FBS and 1% double antibody at 37° C. in a cell incubator containing 5% $CO_2$;

IOSE80 (human normal ovarian epithelial cells): the cells were incubated in a 1640 medium containing 10% FBS and 1% double antibody at 37° C. in a cell incubator containing 5% $CO_2$;

OV2008 (human ovarian cancer cells): the cells were incubated in a DMEM medium containing 10% FBS and 1% double antibody at 37° C. in a cell incubator containing 5% $CO_2$;

PANC1 (human pancreatic cancer cells): the cells were incubated in a DMEM medium containing 10% FBS and 1% double antibody at 37° C. in a cell incubator containing 5% $CO_2$;

2. Extraction of Nucleoprotein

Cell collection: each cell was washed in a 100 mL flask with 1×PBS once, digested with a digestion solution (0.02% EDTA and 0.05% trypsin), added a complete medium containing 10% FBS to terminate digestion; the cells were mixed well by pipetting, centrifuged at 2,000 rpm for 5 min, resuspended and rinsed in PBS once, and a supernatant was discarded completely.

450 μL of 0.4% NP-40 (containing protease inhibitor cocktail) was added, vortexed for 5 min, and centrifuged at 5,000 rpm at 4° C. for 10 min, the obtained pellets were the nucleus; 300 L of 0.1% NP-40 (containing protease inhibitor cocktail) was added to the pellets, mixed by flicking, centrifuged at 5,000 rpm at 4° C. for 10 min, a supernatant was discarded completely, 200 μL of RIPA was added, mixed well and dispersed, and nucleoproteins were obtained by freezing and thawing once at −80° C.

3. WB Detection of an Expression Level of Hydroxylated WSTF (1) A SDS denaturing 10% polyacrylamide gel was prepared (lower separation gel, single-sided):

TABLE 6

Formulation of 6% polyacrylamide gel

| Component | Volume |
|---|---|
| DDW | 5.8 mL |
| 40% acrylamide | 1.5 mL |
| 1.5M Tris-Cl (pH = 8.8) | 2.5 mL |

TABLE 6-continued

Formulation of 6% polyacrylamide gel

| Component | Volume |
|---|---|
| 10% SDS | 100 μL |
| 10% ammonium persulfate | 100 μL |
| TEMED | 4.0 μL |

After mixing, the gel was quickly poured to about ⅔ of the total height of the glass plate, and then 1 mL of water-saturated n-butanol was added on the top of the gel to ensure the smoothness of the upper layer of the gel, and allowed to stand for the gel to solidify.

(2) A SDS denaturing 5% polyacrylamide gel was prepared (upper stacking gel, single-sided)

TABLE 7

Formulation of 5% polyacrylamide gel

| Component | Volume |
|---|---|
| DDW | 2.225 mL |
| 40% acrylamide | 375 μL |
| 1.5M Tris-Cl (pH = 6.8) | 380 μL |
| 10% SDS | 30 μL |
| 10% ammonium persulfate | 30 μL |
| TEMED | 3.0 μL |

After mixing, the gel was quickly poured until the glass plate was filled, the comb was inserted, and allowed to stand for the gel to solidify. Before electrophoresis, the comb was removed, the gel was placed in a 1×Tris-glycine running buffer, and the sample wells were blown out with a syringe needle.

(3) The protein sample was mixed with a 5× loading buffer (containing β-mercaptoethanol), boiled for 5 min to denature, and then treated in an ice bath for 5 min. An appropriate amount of protein sample was loaded and subjected to SDS denaturing 10% polyacrylamide gel electrophoresis until a target protein was effectively separated and the electrophoresis was terminated.

(4) After electrophoresis, the gel was taken out and placed in a special sandwich clip for transfer, the gel was placed in the negative electrode, the PVDF membrane was placed in the positive electrode, and the membrane was transferred at a constant current of 350 mA in a transfer buffer for 2 h at 4° C., such that proteins in the gel were transferred to PVDF membranes to form blots.

(5) The membrane was put in 1×Blotto, and shaken at room temperature for 2 h.

(6) The membrane was cut according to a blotting position of the protein, placed in Blotto containing the corresponding primary antibody (purified polyclonal antibody Ab1 prepared in Example 2), and shaken at 4° C. overnight.

(7) The membrane was placed in the 1×TBST, shaken, and rinsed for 5 min, a total of 4 times.

(8) The membrane was placed in Blotto containing the corresponding secondary antibody (HRP-labeled goat anti-rabbit IgG antibody) for 1.5 h at room temperature.

(9) The membrane was placed in the 1×TBST, shaken, and rinsed for 5 min, a total of 4 times.

(10) The membrane was placed in Western Lightning™ Chemiluminescence Reagent for 30 sec.

(11) The membrane was immediately placed in an exposure box, and a photosensitive film was exposed for 1 min in a dark room, and then developed and fixated.

(12) The film was photographed with a LabWorks™ gel imaging and analysis system, and the brightness values of bands of each group were analyzed. The method included: a ratio of a target band brightness value of each sample to a band brightness value of the corresponding LMNB1 (internal reference) was calculated to obtain a corrected target band brightness value. Taking the control group as a standard value 1, and a histogram was drawn, the results were shown in FIG. 12.

Figure 12:
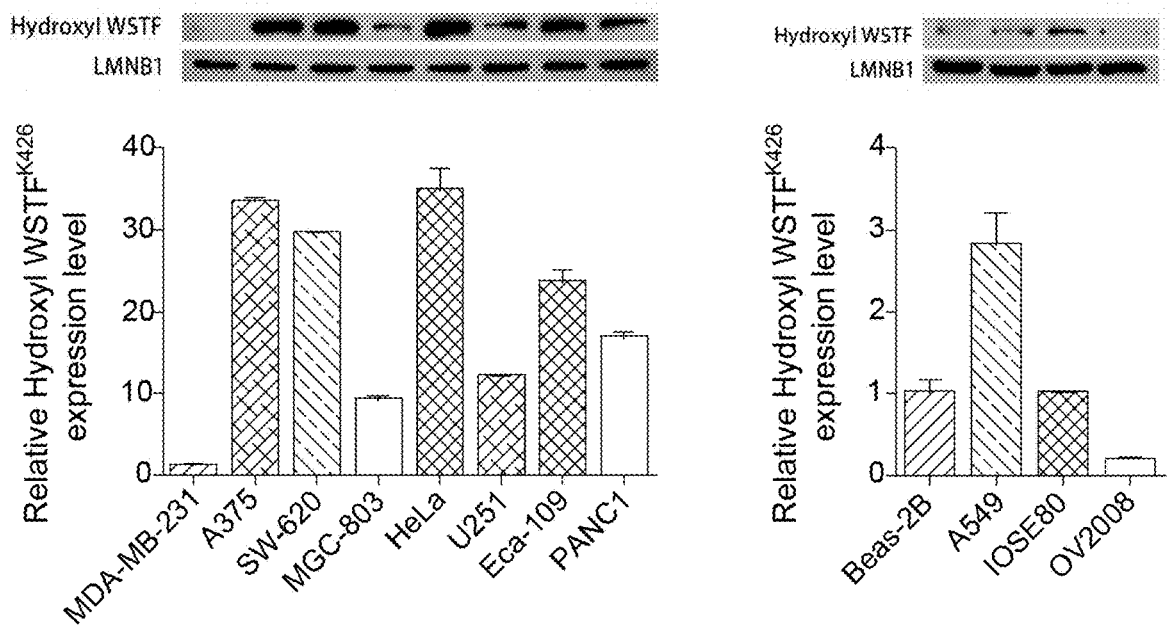
FIG. 12 shows the results of WB detection on expression levels of BAZ1B_K426hy in various tumor cells.

It was seen from FIG. 12 that the expression level of BAZ1B_K426hy in human normal cells was almost stable, while the expression level of BAZ1B_K426hy in tumor cells was significantly different from that in the normal cells. It indicated that the occurrence of tumors could be diagnosed by detecting the expression level of BAZ1B_K426hy.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for preparing a product for evaluating a risk of a tumor, comprising the steps of:
   (1) coupling polypeptide A and polypeptide B of an immunogenic polypeptide to KLH separately to obtain two coupled polypeptides;
   (2) mixing two solutions of the two coupled polypeptides in a volume ratio of (1-2):(1-2) to obtain a mixed solution of the two coupled polypeptides;
   (3) immunizing an animal with the mixed solution of the two coupled polypeptides, collecting serum of the immunized animal, and purifying the serum to obtain an anti-BAZ1B_K426hy polyclonal antibody;
   (4) including the anti-BAZ1B_K426hy polyclonal antibody in the product for evaluating a risk of a tumor;
   wherein BAZ1B_K426hy is a protein modified by hydroxylation (hy) of a Lys426 residue of WSTF (BAZ1B);
   wherein polypeptide A has the sequence of SKSPK-hydroxyl K-GLKTP (SEQ ID NO: 1) and polypeptide B has the sequence of NSKSPK-hydroxyl K-GLKTPK (SEQ ID NO: 2); and
   wherein the tumor is selected from lung cancer and ovarian cancer.

2. The method according to claim 1, wherein the product is selected from the polyclonal antibody, a medicament comprising the polyclonal antibody, and a kit comprising the polyclonal antibody.

* * * * *

SEQUENCE LISTING

```
Sequence total quantity: 3
SEQ ID NO: 1            moltype = AA  length = 11
FEATURE                 Location/Qualifiers
source                  1..11
                        mol_type = protein
                        note = linker sequence
                        organism = synthetic construct
SEQUENCE: 1
SKSPKKGLKT P                                                    11

SEQ ID NO: 2            moltype = AA  length = 13
FEATURE                 Location/Qualifiers
source                  1..13
                        mol_type = protein
                        note = linker sequence
                        organism = synthetic construct
SEQUENCE: 2
NSKSPKKGLK TPK                                                  13

SEQ ID NO: 3            moltype = AA  length = 13
FEATURE                 Location/Qualifiers
source                  1..13
                        mol_type = protein
                        note = non-modified control polypeptide
                        organism = synthetic construct
SEQUENCE: 3
NSKSPKKGLK TPK                                                  13
```